United States Patent [19]

Karr, Jr. et al.

[11] Patent Number: 4,891,219
[45] Date of Patent: Jan. 2, 1990

[54] METHOD FOR IMMUNIZATION AGAINST AND TREATMENT OF INFECTION BY ECTOPARASITES AND ENDOPARASITES

[75] Inventors: Stephen L. Karr, Jr.; Elizer Benjamini, both of Davis; Robert J. Scibienski, Woodland; Stephen Grimes, Davis, all of Calif.

[73] Assignee: Aphton Corporation, Woodland, Calif.

[21] Appl. No.: 96,699

[22] Filed: Sep. 14, 1987

Related U.S. Application Data

[63] Continuation-in-part of Ser. No. 839,892, Mar. 14, 1986, Pat. No. 4,814,170.

[51] Int. Cl.$^4$ .................... A61K 37/24; A61K 39/395
[52] U.S. Cl. ............................... 424/85.8; 424/85.91; 424/88; 514/2; 514/12; 514/885; 530/387; 530/389; 530/391; 530/399; 530/402; 530/403; 530/808; 530/810; 530/811; 530/812; 530/816
[58] Field of Search .............. 424/85, 88, 85.8, 85.91; 514/2, 12, 885; 530/387, 389, 391, 399, 402, 403, 808, 810-812, 816

[56] References Cited

U.S. PATENT DOCUMENTS

| | | | |
|---|---|---|---|
| 3,395,218 | 7/1968 | Silverman | 424/88 |
| 3,746,490 | 7/1973 | Marsland et al. | 514/136 |
| 3,874,533 | 4/1975 | Carr et al. | 414/3 |
| 4,036,987 | 7/1977 | Thompson et al. | 514/671 |
| 4,374,853 | 2/1983 | Workman | 514/506 |

OTHER PUBLICATIONS

Atassi et al., *Biochemical, Biophys. Acta,* 670, 1981, pp. 300–302.
Kennedy et al., *Clinic Chemica Acta* 70, 1976, pp. 1–31.
Senier et al., *Clin. Chem.,* 27(1), 1981, pp. 1797–1806.
Connat et al., *CA,* vol. 100, #189112k.
Borst et al., Science, vol. 178, Oct. 27, 1972, pp. 418–419.
Lauer et al., Experientia 30/3 (1974), pp. 558–560.
Lauer et al., Experientia 30/3 (1974), pp. 560–562.
Borst et al., Steroids, vol. 24, No. 5, Nov. 1974, pp. 637–656.
Glaun, Proceedings of a Workshop on the Ecology and Control of Ectoparasites on Bovines in Latin America, (1975).
Koolman et al., Biosynthesis, Metabolism and Mode of Action of Invertebrate Hormones, pp. 323–330, (1984).
Hirn et al., Progress In Ecdysone Research, (1980).
Reum et al., Insect Biochem., vol. 9, pp. 135–142, (1979).
Maroy, FEBS Letters, vol. 81, No. 2, pp. 319–322, (1977).
Horn et al., Insect Physiol., vol. 22, pp. 901–905, (1976).
Strambi et al., Eur. J. Biochem. 118, pp. 401–406, (1981).
Baehr et al., FEBS Letters, vol. 69, No. 1, pp. 123–128.
Dennis, International Journal for Parasitology, vol. 7, pp. 171–179, (1977).
Boisvenue et al., Experimental Parasiotology, 42, 67–72, (1977).
Hitcho et al., The J. of Parasitology, vol. 57, No. 4, pp. 787–793, (1971).
Dennis, Comp. Biochem. Physiol. vol. 53A, pp. 53–56, (1976).
Davey, Biochemistry of Parasites and Host—Parasite Relationships, pp. 359–375 Van den Boshe, Ed. Elsevier Mango, Tick Borne Diseases and Their Vectors, pp. 35–37,
Davey, International Journal for Parasitology, vol. 1, pp. 61–66, (1971).
Hansen et al., Experientia 27, 7 859–860, (1971).
Bottjer et al., Comp. Biochem. Physiol. vol. 82B, No. 1, pp. 99–106, (1985).
Feldmesser et al., Experientia 32/4 pp. 466–467, (1976).
Goodman & Gilman's, The Pharmacological Basis of Therapeutics, 6th Ed., pp. 1013–1079, (1980).
Van Nostrand's Scientific Encyclopedia, 6th Ed., pp. 1620–1625, (1983).
F. W. Douvres et al., Veterinary Parasitology, I, pp. 195–205, (1980).
G. H. Glassburg et al., Proc. Helm. Soc. Wash., 50, pp. 62–68, (1983).
Khalil et al., J. Med. Entomol., vol. 21, No. 5:561–566, (1984).
Khalil et al., J. Med. Entomol, vol. 21, No. 2:188–193, (1984).
Campbell et al., Acarology VI, vol. 1, pp. 393–399, (1984).
Ampleford et al., General and Comparative Endocrinology 63, 353–361, (1986).
Spindler et al., Z Parasitenkd, 72:837–841, (1986).
Mehlhorn et al., Parasitenkd 72:843–845, (1986).
Klaus et al., Cellular Immunology 14, 226–241, (1974).

*Primary Examiner*—Garnette D. Draper
*Attorney, Agent, or Firm*—Dimitrios T. Drivas

[57] ABSTRACT

This invention relates to a method for the active or passive immunization of a vertebrate against ectoparasites and endoparasites, and a method of treating a vertebrate host infected by ectoparasites or endoparasites, comprising administering to the vertebrate an immunogen comprising one or more endocrine products of ectoparasites and endoparasites, coupled with an immunogenic carrier, or administering to the vertebrate, monoclonal antibodies capable of binding to the native form of the endocrine product.

11 Claims, No Drawings

METHOD FOR IMMUNIZATION AGAINST AND TREATMENT OF INFECTION BY ECTOPARASITES AND ENDOPARASITES

This application is a continuation-in-part of copending application U.S. Ser. No. 839,892 filed on Mar. 14, 1986 now U.S. Pat. No. 4,814,170.

BACKGROUND OF THE INVENTION

This invention relates to the use of invertebrate growth regulators neurohormones and other invertebrate endocrine products as vaccine components to actively immunize a vertebrate against ectoparasites and endoparasites, and as medicaments to treat a vertebrate infected by said parasites. In another embodiment of the invention anti-parasitic growth regulator antibodies are used to actively or passively immunize a vertebrate against and to eliminate infection by ectoparasites and endoparasites.

Conventional attempts to prevent, or rid a host of, infection by ectoparasites and endoparasites, (hereinafter also referred to as target parasites) have involved treatment of a susceptible or infected host (e.g., mammal) with antihelmintic chemicals [see generally, Goodman and Gilman's, *The Pharmacologicol Basis for Therapeutics*, 6th Ed., pp. 1013-79 (1980)]. For example, U.S. Pat. No. 3,746,490 refers to a method for controlling first instar bot larvae and endoparasites in horses comprising applying a paste containing dimethyl-1- dichlorovinyl phosphate into the mouth of a horse; U.S. Pat. No. 3,879,533 refers to the control of endoparasitic nematodes by 3-phenyl-5-(halo-, alkylthio- or alkoxy)-isoxazoles; U.S. Pat. No. 4,036,987 refers to the control of nematodes and other helminths using secondary and tertiary straight end branched chain amides and amines; and U.S. Pat. No. 4,374,853 refers to a method for controlling mammalian ectoparasites, such as fleas and ticks, using an aqueous antiseptic liquid. Typically these treatments are characterized by various undesirable side effects, such as short periods of sensitivity, toxic build-up of chemicals, a need to re-treat animals and the development of resistance to chemicals by the targeted parasites.

In view of the disadvantages of such therapies, various other methods of protecting mammals from ectoparasitic and endoparasitic infection have been attempted. For example, U.S. Pat. No. 3,395,218 refers to a method of immunization using nematode surface antigens formed from the ex-sheathment of larvae. More recently, attempts have been made to use ecdysone or juvenile hormones and their analogues to disrupt directly the development of helminth endoparasites. For example, when juvenile hormones are administered to the infected host during metamorphosis (larvae into adult) the adult endoparasites produced are deformed and lack the capacity for further development and soon die [see generally, Van Nostrand's *Scientific Encyclopedia*, 6th Ed. pp. 1620-25 (1983); F. W. Douvres et al., "In Vitro Cultivation of *Ostertagia ostertagi*, The Medium Stomach Worms of Cattle. II. Effect of Insect-Growth-Disrupting Amines and Amides on Development," *Veterinary Parasitology*, 1, pp. 195-205 (1980); G. H. Glassburg et al., "Juvenoid effects on *Niopostronovlus brasiliensis* and *Heterodera glycines* " (Nematoda), "*Proc. Helm. Soc. Wash.* 50, pp. 62-68 (1983)]. However, such treatment is not very reliable because effectiveness is limited to the relatively short period of metamorphosis; if the juvenile hormones are applied before or after this period, they are ineffective. Furthermore, such treatment would have to be repeated frequently and, because of inefficient tissue distribution in the infected host, may not even reach and be absorbed by the infected tissue.

SUMMARY OF THE INVENTION

The present invention relates to a method of actively or passively immunizing a vertebrate against infection by ectoparasites or endoparasites and a method of treating a vertebrate infected by ectoparasites or endoparasites, comprising administering to the vertebrate an effective amount of an immunogen comprising an endocrine product of the ectoparasite or endoparasite coupled with an immunogenic carrier. According to the present invention, a susceptible or compromised vertebrate is immunized, or treated, using a vaccine or medicament, formed from a preparation of parasite hormones. The vaccines or medicaments of the present invention may be used to induce an active immune response in a potential vertebrate target or host so that specific antibodies are raised against the targeted parasitic hormone that will bind to and block the activity of that hormone so that the parasites fail to develop, and then die. The present invention also concerns a method for preparing the vaccine or medicament which comprises preparing and selecting immunogens which are capable of generating antibodies that react with the free native hormone and are thus biologically effective.

Alternatively, monoclonal antibodies, prepared in vitro, which are specific for the targeted free native form of the parasitic hormone may be administered directly to passively immunize the vertebrate.

The present invention also comprises a vaccine or medicament comprising the aforementioned immunogens and a pharmaceutically acceptable carrier. The inventive composition may also comprise a vehicle (e.g., sterile saline) and optionally may also comprise a suitable adjuvant (e.g., alum).

DETAILED DESCRIPTION OF THE INVENTION

In the description of the invention, the following terms are set forth:

ECTOPARASITE -- An ectoparasite is a parasite which lives on the outside of the body of the host. Examples of ectoparasites are insects of the order Siphonaptera, commonly known as fleas, and the blood-sucking acarid parasites of the order Acarina, commonly known as ticks and mites.

ENDOPARASITE -- An endoparasite is a parasite that lives within the body of its host. Examples of endoparasites are any of the families of parasitic flatworms (Phyla Platyhelminthes, e.g., Trematoda and Cestoda), roundworms (Aschelminthes, e.g., Nematoda), and the larval forms of certain flies that cause myiasis.

ENDOCRINE PRODUCT -- As used in this description, an endocrine product includes natural hormones, hormone-like polypeptides or fragments thereof possessing the antigenic characteristics of the targeted hormone.

JUVENILE HORMONES -- Juvenile Hormones (JH) are organic compounds involved in the growth, development and reproduction of insects, which are present in insects during the greater part of their development. As used in this description, "JH" refers to acyclic sesquiterpenes, which are secreted by the "corpus allatum" gland located behind the brain [see J. C. Baeher et al., "A Simple And Sensitive Insect Juvenile Hormone Using An Iodinated Tracer," *FEBS Letters*, 69, pp. 123-28 (1976)].

Juvenile Hormones are simple hapten antigens. $JH_3$, for example, is a 16 carbon lipidlike hydrophobic molecule, approximately 14 angstroms in length. There are two slightly polar groups, the epoxide and methyl ester, at either end that provide the weak hydrophilicity that the molecule exhibits. The different forms of JH vary only by the length of the carbon side chains at positions 3, 7, 11 of the molecule. They are usually either methyl and/or ethyl groups, depending upon the JH type. Over 4000 analogs of JH have been synthesized. Many of these analogs may be useful in the methods of this invention.

JH are known to control development in insects from larvae to adult stages. [See W. W. Doane, *Development Systems*, 2, pp. 291–497 (1973)]. In the adult insect, JH are secreted again and act as gonadotropic hormones by stimulating vitellogenesis and activities of the accessory glands [see F. Engelmann, *The Physiology of Insect Reproduction* (1970)]. A similar control of development and reproduction has been indicated for nematodes [W. P. Rogers, "Juvenile and Moulting Hormones From Nematodes", *Parasitology*, 67, pp. 105–13 (1973)].

ECDYSONE -- Ecdysone is a molting hormone, which initiates the moulting process and induces a larval molt with a high JH titer [see Peter Maroy et al., "Rapid Heterologous Haptene Radioimmunoassay For Insect Moulting Hormone," *FEBS*, 81, pp. 319-22 (1977)]. As used in this application, the term ecdysone includes both alpha-ecdysone and beta-ecdysone, which is commonly known as either ecdysterone or 20-hydroxy ecdysone.

PEPTIDE HORMONES -- Peptide hormones are a diverse group of hormones, made up of covalently linked amino acids. As used in this application, the term peptide hormones includes, but is not limited to, proctolin, an insect neurotransmitter, and adipokinetic hormone, a hormone which controls fat metabolism in insects.

IMMUNIZATION -- The process for eliciting a humoral immune response by an antigen or hapten, i.e., active immunization; or supplementing the body's immune system by administering antibodies formed to that antigen or hapten i.e., passive immunization.

The present invention relates to a process for active or passive immunization against parasites and treatment of a vertebrate compromised by parasitic infection. The process comprises administering to a potential target or compromised vertebrate host, an endocrine product of ectoparasites or endoparasites which has been conjugated to an immunogenic carrier. Alternatively, the process comprises the step of administering preformed antibodies to a target or compromised host by oral or parenteral route. The resultant vaccine or medicament can then be used to elicit an active or passive immune response against the target parasite.

This invention takes advantage of the need of the target parasites to pass through developmental stages (molts) in the host. These molts are controlled, in part, by hormones. Vaccination of the host with immunogens comprising these hormones results in the production of a host immune response that blocks the activity of these parasitic hormones and causes a failure of the parasite to develop and its subsequent death.

Metazoan parasites which contain target hormones potentially useful in the practice of the present invention include representatives of the Phyla Platyhelminthes (e.g., Trematoda and Cestoda), Aschelminthes (e.g., Nematoda), and Arthropoda (e.g., Insecta).

Parasitic hormones demonstrated to be present in the aforementioned metazoan parasites and potentially useful as immunogens in the vaccines of the present invention include the steroids alpha-ecdysone and beta-ecdysone; the terpenoid juvenile hormones (JH), e.g., $JH_0$, $JH_1$, $JH_2$ and $JH_3$, and their structural analogues; and several peptide hormones of varying structure, including shrimp red pigment concentrating hormone, proctolin, adipokinetic hormone, Drosophila paragonial peptide, and their structural analogues.

Several linking (conjugation) methods for linking the hormone to an immunogenic carrier are known to those skilled in the art of preparing conjugates for immunoassays, for example. They include, for example, the known carbodiimide method (see below, Examples 1, 2 and 4) for coupling alpha-ecdysone or beta-ecdysone and the juvenile and peptide hormones to a carrier and the known carboxymethoxylamine method (see below, Example 3) for coupling beta-ecdysone to a carrier. The appropriate linking method is used to prepare an activated hormone intermediate. The intermediate is then linked with a suitable protein carrier, such as, but not limited to, Keyhole Limpet Hemocyanin (KLH), Tetanus Toxoid (TT), Diptheria Toxoid (DT), Bovine Serum Albumin (BSA), or Human Serum Albumin (HSA) to produce an immunogen.

The immunogenic complexes produced by coupling of the anti-parasitic endocrine product and an immunogenic carrier according to the methods of this invention are useful in a variety of compositions and methods for anti-parasitic vaccination and treatment. More particularly, they can be useful in anti-endoparasitic and anti-ectoparasitic vaccination and methods of treatment.

Administration of such immunogens, or pharmaceutically acceptable derivatives thereof, may be via any of the conventionally accepted modes of administration of agents which exhibit immunogenicity against ectoparasites and endoparasites. These include parenteral administration, such as subcutaneous, intramuscular or intravenous injection, or non-parenteral (oral) administration.

The compositions used in these therapies may also be in a variety of forms. These include, for example, solid, semi-solid and liquid dosage forms, such as powders, liquid solutions or suspensions, suppositories, and injectable or infusable solutions. The preferred form depends on the intended mode of administration and therapeutic application.

The compositions also will preferably include conventional pharmaceutically acceptable carriers and may include other medicinal agents, carriers, adjuvants, excipients, etc., e.g., human or bovine serum albumin or plasma preparations. Preferably, the compositions of the invention are in the form of a unit dose and will usually be administered one or more times a day. The amount of active compound administered as a vaccination or as a medicament at one time, or over a period of time, will depend on the subject being treated, the manner and form of administration, and the judgment of the treating physician or veterinarian. However, an effective dose may be in the range of from about 1 ng to about 1 mg of hormone-protein carrier conjugate, preferably about 100 μg to about 500 μg; it being recognized that lower and higher doses may also be useful.

Accordingly, this invention provides a method of vaccination and a method of treatment against parasitic infection in vertebrates including humans, comprising the administration of an immunologically effective amount of a compound of the invention or its immunologically acceptable derivatives. The hormone-carrier conjugates of the present invention, prepared as described above, may be used to immunize humans, dogs, cats, cows, sheep, swine, horses, or other vertebrates by injecting a dosage form of the conjugate, preferably in an aqueous vehicle along with a suitable adjuvant such as alum or an acceptable bio-degradable oil vehicle, with or without an acceptable adjuvant such as MDP (muramyl dipeptide).

In certain embodiments of the invention more than one immunogen, each immunogen comprising a different endocrine product, may be administered to the vertebrate to immunize against or treat the infection of a parasite or parasites. For examPle, immunologically effective amounts of two different immunogens, the first comprising juvenile hormone conjugated to a protein carrier, the second comprising beta-ecdysone conjugated to a protein carrier may be administered together to treat an animal for infection of a parasite, e.g. *O. moubata*.

Alternatively, a cocktail of monoclonal or polyclonal antibodies comprising an immunologically effective amount of antibodies formed to a first hormone, e.g. juvenile hormone and an immunogically effective amount of antibodies formed to a second hormone, e.g. beta-ecdysone may be administered to an animal to passively immunize it against or to treat it for infection by an endoparasite or ectoparasite.

Antibodies induced by the hormone-protein conjugate of this invention may be quantitated by suitable serologic assay such as enzyme linked immuno-sorbent assay (ELISA) or radioimmunassay (RIA) that is capable of specific detection of anti-hormone antibody. Such as assay may detect polyclonal antibodies or monoclonal antibodies (produced by standard hybridoma methods) directed against the hormone. The quantitation of said antibodies provides a measure of the immune status of the vaccinated animal(s). An antibody titer obtained for example, by end point dilution of $\geq 1:1000$ dilution of the ELISA assay is indicative of an immune response that will provide protection against challenge with the appropriate parasite.

It has been discovered that in in vitro immunologic assays that two types of antibody specificities are generated by the hormone-protein conjugates. One type of specificity, (Type 1) recognizes both nonconjugated i.e., the free native hormone or endocrine product, and conjugated forms of the antigen, i.e., hormone bound to carrier protein. The other specificity (Type 2) recognizes only the conjugated form of the hormone or endocrine product as it is bound to the protein carrier.

The Type 1 antibodies bind the free native form of the endocrine product or hormone both in vitro and in vivo as it occurs in the target parasite and consequently induce a biologic effect in the target parasite. The Type 2 antibodies do not bind the native endocrine product in vitro and thus do not bind the native endocrine product in vivo, i.e. Type 2 antibodies are biologically irrelevant.

In a typical immune response in the instance of juvenile hormone it appears that Type 2 antibodies seem to be preferentially produced over Type 1 antibodies. It is therefore one object of the present invention to provide for vaccines or medicaments comprising immunogens that are capable of eliciting Type 1 antibodies in the host vertebrates that bind to the native form of the endocrine product and thus have a biological effect on the parasite This object can be achieved by engineering the immunogen so that it induces a Type 1 high level response The methods of the invention for engineering the immunogen are described in the examples and include such techniques as selecting the carrier proteins bound to the endocrine product for enhanced Type 1 response; providing spacer molecules to the hormone protein conjugate to alter the spatial presentation of the antigen, e.g. linking $JH$ in a 1:1 molecular ratio to a non-immunogenic peptide; conjugating analogs of the hormone in addition to the hormone to the protein carrier; providing for the optimum density of hormone haptens on the protein carrier thus altering the way in which the hormone hapten is presented to the hormone specific B lymphocytes and; producing internal image anti-idiotypic antibodies of the parasite hormone which when used in the immunization elicit a predominantly Type 1 response.

In another embodiment of the invention the host vertebrate can be passively immunized with Type 1 monoclonal or polyclonal antibodies that are capable of binding the native form of the endocrine product thus having a biological effect on the target parasite. These antibodies may be prepared by any method known to those skilled in the art, it being essential to this embodiment of the invention that the antibodies be selected for their Type 1 activity, e.g. screening of hybridomas producing monoclonal antibodies, or affinity purification of polyclonal antibodies.

The vaccines and medicaments of the present invention may be used to immunize against or treat the infection of any invertebrate endoparasite or ectoparasite. Examples of such endoparasites and ectoparasites are the following: organisms of the phylum Aschelminthes, class Nematoda, family, Oxyrudidae e.g. genus Enterobius; family Strongyloididae, e.g. genus Strongyloides; family, Ancylostomatidae, e.g. genera, Ancylostoma, Necator; family Strongylidae, e.g. genera Strongylus, Oesphagastromum, Chabertia, Ternidens; family Trichostrongylidae, e.g. genera, Cooperia, Haemonchus, Ostertagia, Nematodirus; family, Metastrongylidae e.g. genera, Dictycaulus, Metastrongylus; family, Heterakidae, e.g. genus Heterakis; family Ascarididae, e.g. genera Ascaris, Toxascaris, Toxocara; family Onchocercidae, e.g. genera Bruqia, Wuchereria, Dirofilaria, Loa, Onchocerca; family Trichuridae, e.g. genus Trichuris; family Trichinellidae, e.g. genus, Trichinella; organisms of the phylum Platyhelminthes, class Trematoda, family Fasciolidae, e.g., genus Fasciola; family Dicrocoelidae, e.g. genus Dicrocoelium; family Opisthorchiidae, e.g. genus Opisthorchis; family Schistosomatidae, e.g. genus, Schistosoma; class Cestoda, family Anoplocephalidae, e.g. genus Monezia; family Dilepididae, e.g. genus, Diovlidium; family Hymenolepididae, e.g. genus Hymenolepis; family Taeniidae, e.g. genera, Taenia, Echinococus; and ectoparasites and endoparasites of the phylum Arthropoda, class Insecta, family, Ceratopogonidae, e.g. genus Culicoides; family Simulidae, e.g. genus Simulium; family Psychodidae, e.g. genus, Phlebotomus; family Culicidae, e.g. genera Culex, Aedes, Anooheles; family Tabanidae, e.g. genus Chrysops; family Oestridae, e.g. genera Gasterophilus, Oestrus, Hypoderma, Dermatobia; family Anthomyidae, e.g. genera Stomoxys, Glossina; family Tachinidae, e.g. genera Lucilia, Calliphora, Phormia, Chrysomyia, Callitroga, Cordylobia; family, Sarcophagidae, e.g. genera Sarcoghaga, Wohlfartia; family Hippoboscidae e.g. genus, Melaphagus; family Triatomidae, e.g. genera Triatoma, Panstrongulus, Rhodnius; family Haematopinidae, e.g. genus, Haematopinus; family Linognathidae, e.g., genus Linognathus; family Pediculidae, e.g., genera Pediculus, Phtirus; family Tungidae, e.g. genus Echidnoohaoa; family Pulicidae, e.g., genus Ctenoceohalides; class Arachnida, family, Dermanyssidae, e.g., genera Dermanvssus, Ornithonyssus; family Argasidae, e.g. genera Arous, Otobius; family Ixodidae, e.g. genera Ixodes, Boophilus, Haemaphysalis, Dermacentor, Amblyomma; and family Sarcoptidae, e.g. genus Sarcootes. Immunogens and antibody compositions useful as vaccines or medicaments in vertebrates for treatment of or prevention of infection by any of the above listed organisms can be prepared according to the methods of this invention as described herein. In each case a suitable endocrine product of the parasite organism is used to produce an immunogen according to the methods of the invention. In certain embodiments where immunogens that are capable of eliciting a Type 1 biologically effective response we preferred, the Type 1 immunogens may be selected as described herein. The immunogens or antibody vaccines produced with the immunogen may be used in the vaccine immunization or treatment methods of the invention.

In order that the invention described herein may be more fully understood, the following examples are set forth. It should be understood that these examples are for illustrative purposes only, and are not to be construed as limiting this invention in any manner.

EXAMPLE 1

In this example, we illustrate the preparation of one embodiment of an immunogen of this invention. The immunogen was prepared according to a modification of the method of J. C. Baehr et al. ["A Simple and Sensitive Radioimmunoassay Of Insect Juvenile Hormone Using An Iodinated Tracer", *FEBS Letters*, 69, pp. 123–28 (1976)]. This method may be used for any of the naturally occurring JH. First, we prepared a free acid derivative by subjecting $JH_3$ to alkaline hydrolysis. We dissolved 10 mg of $JH_3$ in 0.25 ml of methanol. We then added 2 ml of methanol/1N NaOH (v/v) to the $JH_3$ and allowed the mixture to react for four hours at room temperature.

We titrated the reaction mixture with 5.0 M HCl to lower its pH to 5.0 and then we lyophilized it. We then extracted the $JH_3$ acid by adding 1 ml of ethyl acetate to the lyophilate. We removed the ethyl acetate with a pipette and then repeated the ethyl acetate extraction. We pooled the ethyl acetate extracts and then centrifuged the pooled extracts at 10,000 ×g to precipitate solids, and then removed the supernatant. We transferred the supernatant to a tared vial and removed the ethyl acetate from the $JH_3$- acid by exposing the solvent to a gentle nitrogen ($N_2$) stream. The solvent evaporated and $JH_3$-acid was deposited as an oily film on the vial wall. The vial was weighed to determine the weight of $JH_3$-acid recovered.

The recovered $JH_3$ derivative was reacted with N-hydroxy- succinimide (NHS) to prepare a NHS-JH activated ester intermediate. We dissolved sufficient molar amounts of NHS and dicyclohexylcarbodiimide (DCCI) in 1.0 ml of tetrahydrofuran (THF) to equal the number of moles of $JH_3$-acid recovered. We then added this solution to the $JH_3$, added a small amount of pyridine, and allowed the reaction to proceed overnight. We then inactivated and removed any unreacted NHS and DCCI by adding a small amount of ECH Sepharose beads to the reaction mixture. We then centrifuged the reaction mixture at 10,000×g to pellet the Sepharose beads and precipitates of dicylohexyl urea and drew off the supernatant. We evaporated off the THF under a nitrogen stream and then added 1.0 ml THF to extract $JH_3$-NHS ester from the resulting solid material. We repeated the evaporation, extraction and evaporation steps.

In order to prepare the coupled $JH_3$-KLH, we dissolved the $JH_3$-NHS ester in 0.25 ml THF and prepared two (2) 0.125 ml aliquots equivalent to 4.0 mg $JH_3$. We dissolved 10 mg of KLH or 20 mg of Bovine Serum Albumin (BSA) in 2 ml of 0.5 M NaCl or 4.0 ml of 0.15 M NaCl, respectively. This mixture was added to each aliquot of activated $JH_3$ and incubated overnight. We then evaporated off the THF under a gentle nitrogen stream and dialyzed the resulting $JH_3$-KLH conjugate against phosphate buffered saline (PBS) to remove unreacted $JH_3$ or other contaminants.

We estimated the number of $JH_3$ molecules attached to each molecule of KLH or BSA by one or more methods known to those skilled in the art including the isotopic dilution method, the TNBS or fluorescamine free amino acid determination method, or the comparison of UV absorption at two wave lengths method (e.g. 260 nm. and 280 nm.). The coupling ratios were expressed in molecules of $JH_3$ coupled per $10^5$ daltons molecular weight of protein e.g. (KLH or BSA). In the conjugation method described above, the number of molecules of $JH_3$ conjugated per $10^5$ daltons molecular weight of protein varies between 28–38 for KLH conjugates and 20–28 for BSA conjugates. By varying the amounts of activated $JH_3$ mixed with the amount of carrier, other coupling ratios varying between less than one to approximately 50 $JH_3$ molecules per $10^5$ daltons molecular weight of protein carrier can be obtained.

EXAMPLE 2

Example 2 illustrates one embodiment of our method of preparing peptide hormone-protein conjugates.

Peptide hormones may be conjugated to a protein carrier by various methods known to the art including carbodiimide, glutaraldehyde, or diazotization methods [see e.g., B. F. Erlanger, "The Preparation of Antigenic HaptenCarrier Conjugates: A Survey," *Methods in Enzymology*, vol. 70, pp. 85–104 (1980)].

We conjugated proctolin and adipokinetic hormones through the carboxy-terminus of the peptide hormone to the carrier protein. We dissolved the peptide hormone in 0.15 M NaCl containing water soluble NHSS and 1-ethyl-3-3-(dimethylaminopropyl carbodiimide) (EDCI). After overnight incubation and stirring, we inactivated the NHSS and EDCI with 0.1 M $Na_2CO_3$ and dissolved the carrier protein in 0.1 M $Na_2CO_3$. We then added 10 mg of carrier protein to 1 mg of peptide and incubated the mixture overnight. We finally separated the conjugate from the other reactants by dialysis against PBS and lyophilized it for storage.

EXAMPLE 3

In this example, we illustrate the conjugation of beta-ecdysone (ecdysterone) to a protein carrier. Our method involves activation of the hormone by formation of an oxime through the double bonded oxygen at carbon 6 [see e.g., Porcheron et al. "Radioimmunoassay Of Arthropod Moulting Hormone: Beta-ecdysone Antibody Production And 125$^I$-iodinated Tracer Preparation", 1976 *FEBS Letters* 61:159–162 which utilizes the oxime intermediate]. This method may also be used for alpha-ecdysone and similar ecdysone analogues.

We dissolved 5 mg of ecdysterone in 600 µl of pyridine containing 2% w/v carboxymethoxylamine. After overnight incubation at an elevated temperature, preferably 50° C., we added benzene to the sample to dilute the pyridine. We then removed the pyridine by drying under a nitrogen ($N_2$) stream. The benzene wash is repeated until the pyridine has been removed.

We added ethyl acetate/30% methanol (10v:1v) to the residue. We removed the organic phase containing the beta-ecdysone, and measured the Optical Density (O.D. 255 nm.) to ascertain the presence of the beta-ecdysone (O.D. =1.80). The ethyl acetate was removed by $N_2$ stream and the residue was reconstituted in tetrahydrofuran (THF) containing N-hydroxysuccinimide (NHS) and dicyclohexylcarbodiimide (DCCI). The latter two reagents may also include their more water soluble forms, N-hydroxysulfosuccinimide (NHSS) and 1-ethyl-3- (3-dimethylaminopropyl carbodiimide) (EDCI).

We then incubated the above reactants for 24–48 hours at room temperature and then added ECH Sepharose beads to inactivate and remove any free NHS (NHSS) or DCCI (EDCI). After adding 10–20 mg of carrier protein (e.g., KLH, BSA) dissolved in 0.1 M $NaPO_4$ buffer, pH 7.5 to the beta-ecdysone-NHS, we stirred overnight. We dialyzed the conjugate against phosphate buffered saline (pH 7.2) and lyophilized it for storage.

As an alternative, a preferred method of conjugation of beta-ecdysone follows the method described by M. A. Delaage, M. H. Hirn and M. L. DeReggi, "Radioimmunoassay of Ecdysteroids," (1982) Methods in Enzymology 84:350–358.

Beta-ecdysone is reacted with succinic anhydride dissolved in 1 ml of dioxane containing 100 µl of triethylamine. The mixture is stirred at 35° C. for 48 hours. The reaction is stopped by the addition of 2 mls of water and the mixture is loaded onto a QAE-Sephadex column (1×30 cm). The column is eluted with about 300 mls of an ionic strength gradient of 0.02 M NaCl and 0.4 M NaCl. The succinylated beta-ecdysone elutes at 0.2 M NaCl and is collected free of other contaminating materials. The beta-ecdysone succinate is desalted by rechromatographing on QAE Sephadex followed by elution with 0.01 M HCl. The product is neutralized with 0.01 M NaOH and lyophilized.

Activation of beta-ecdysone-succinate prior to coupling to the carrier is achieved by forming a mixed anhydride intermediate. Molar equivalents of beta-ecdysone succinate and isochloroformate are mixed together in 400 µl of cold dimethylformamide solvent containing a small amount of triethylamine. The activation reaction is allowed to proceed at 4° C. for 10 minutes, then 10–20 mgs of carrier protein dissolved in 2 mls of dioxane:$H_2O$ (1:1 v/v) is added. The reaction mixture is stirred for one hour and then dialyzed overnight against a suitable buffer such as 0.1 M PBS.

The number of beta-ecdysone molecules coupled per $10^5$ daltons molecular weight of protein can be adjusted by varying the amounts of activated beta-ecdysone per amount of protein carrier. The actual number coupled to the carrier is estimated by any of the assays listed in Example 1 that are used to estimate $JH_3$ coupling.

EXAMPLE 4

Example 4 illustrates our in vivo results using the JH immunogen prepared in Example 1 above.

We vaccinated fifty mice, four times at approximately one month intervals with 500 µg of Juvenile Hormone Immunogen ($JH_3$—KLH) per injection. The initial injection was given intraperitoneally in Freunds Complete Adjuvant. The three remaining injections were given in physiologic saline alternating between subcutaneous and intraperitoneal sites. Two weeks after the second, third and fourth injections, blood was drawn from each mouse and the serum collected. Each serum was assayed for anti-JH anti-bodies utilizing an ELISA technique and $JH_3$—BSA (Bovine Serum Albumin) as antigen. The spleen from one immunized mouse, which was selected by antibody titer, was removed and its cells were fused to a mouse plasmacytoma line according to published hybridoma methods [B. B. Mishell and S. M. Shiigi, *Selected Methods in Cellular Immunology*, San Francisco (1980)]. Hybrids producing monoclonal antibodies with specificity for $JH_3$ were cloned and grown according to published procedures. Monoclonal antibodies were collected in quantity from expanded cell cultures.

For testing against *C. eleoans*, we pooled together the sera collected from the mice and used it at 1:200, 1:2,000 or 1:20,000 dilution. For testing monoclonal antibodies, we used 3 µg of single anti-$JH_3$ monoclonal antibody (Mab) that was known to bind to free $JH_3$ hormone. We tested the antibodies by incubating eggs of *C. eleoans* (10 eggs×5 replicates) in 96 well culture plates containing either 50 µl of diluted serum or 3 µg of Mab. The percent mortality of larvae hatching from the eggs, the percentage of the surviving larvae developing to adults, and the egg production of these adults in the presence of the $JH_3$ specific antisera or Mab were compared to the same percentages obtained for worms exposed to sera or a Mab not specific for $JH_3$.

Table 1 demonstrates the larvacidal activity of the anti-$JH_3$ pooled sera and Mab on the *C. elecans* larvae hatching from eggs. It depicts the percentage of larvae of *C. eleoans* surviving exposure to $JH_3$ specific antibodies. In both instances, less than 50% of the larvae survive exposure to antibody (only at 1:200 dilution of pooled sera).

TABLE 1

| Antibody source | % Larvae surviving for +2 days exposure to Antibody |
|---|---|
| 1:200 pooled serum no anti-$JH_3$ activity | 100% |
| 1:20,000 pooled serum anti-$JH_3$ activity | 100% |
| 1:200 pooled serum, anti-$JH_3$ | 47% |
| 3 ug Mab, no anti-$JH_3$ activity | 100% |
| 3 ug Mab, anti-$JH_3$ activity | 42% |

Table 2 describes the effect of anti-$JH_3$ pooled sera and Mab on the further development of larvae not killed by antibody (see Table 1). It depicts the percentage of larvae *C. elegans* developing to adult stage after $JH_3$ specific antibody treatment for two days. Antibody treatment inhibited and/or delayed development of larvae to adults.

TABLE 2

| Treatment | % Developing to Adult (Days required) |
|---|---|
| 1:200 pooled serum no anti-JH$_3$ activity | 98% (1) |
| 1:20,000 pooled serum anti-JH$_3$ activity | 99% (2) |
| 1:20,000 pooled serum anti-JH$_3$ activity | 83% (5) |
| 1:200 pooled serum, anti-JH$_3$ activity | 30% (2) |
| 3 ug Mab, no anti-JH$_3$ activity | 100% (1) |
| 3 ug Mab anti-JH$_3$ activity | 100% (2) |

Table 3 shows the effect of anti-JH$_3$ antibody treatment on egg production by adult worms. It depicts the egg production by surveying adult *C. elegans* 1–3 days after reaching the adult stage. Pooled antibody and Mab reduced egg production at all concentrations tested.

TABLE 3

| | Egg Production as % Control DAY | | |
|---|---|---|---|
| | 1 | 2 | 3 |
| 1:200 pooled serum no anti-JH$_3$ activity | 100% | 100% | 100% |
| 1:20,000 pooled serum anti-JH$_3$ activity | 23% | 55% | 60% |
| 1:2,000 pooled serum anti-JH$_3$ activity | 0% | 15% | 17% |
| 1:200 pooled serum, anti-JH$_3$ activity | 0% | 0% | 10% |
| 3 ug Mab, no anti-JH$_3$ activity | 100% | 100% | 100% |
| 3 ug Mab, anti-JH$_3$ activity | 0% | 17% | 60% |

EXAMPLE 5

For testing against *Nematospiroides dubius* or *Nippostrongylus braisiliensis*, we infected immunized mice with 200–250 infectious stage larvae (L$_3$). At 10 days (*N. dubius*) or 7 days (*N. brasiliensis*) post infection, we euthanized the mice and excised the small intestines. We then compared the worm burdens between JH-immunized and control (KLH only) immunized mice.

Table 4 shows the effect of prior immunization with JH$_1$, JH$_2$ or JH$_3$ on the reduction in worm burdens of mice challenged with 250 larvae of *N. dubius*. The JH immunized mice experienced a statistically significant decrease in the number of worms recovered at +10 days of infection (p= <0.01). The small intestines likewise demonstrated reduced inflammation and other damage due to the presence of the worms.

TABLE 4

| Immunization | Mean Worm Burden + SE | % Reduction Versus Control | Pathology in* Small Intestine |
|---|---|---|---|
| Control (N = 12) | 244 + 20 | — | +++ |
| JH$_1$ (N = 12) | 144 + 16 | 41% | + |
| JH$_2$ (N = 12) | 159 ± 12 | 35% | + |
| Control (N = 9) | 208 ± 12 | — | +++ |

TABLE 4-continued

| Immunization | Mean Worm Burden + SE | % Reduction Versus Control | Pathology in* Small Intestine |
|---|---|---|---|
| JH$_3$ (N = 9) | 139 ± 11 | 33% | + |

+ indicates the relative pathology of the small intestine.
The pathology of the small intestine was determined by assaying for a significant decrease in intestinal mucosal secretions by spectrophotometic determination of gut fluid and by counting mucosal cysts. Immune animals had fewer cysts and a higher percentage of dead worm larvae within the cysts.

Table 5 demonstrates the effect of prior immunization with JH$_3$ on the reduction in worm burdens of mice challenged with 200 larvae of *N. brasiliensis*. At 7 days post infection, immunized mice experienced a statistically significant (p= <0.002) reduction in intestinal worm burden. More larvae were recovered from the lungs of immunized mice, indicating their entrapment there.

TABLE 5

| Immunization | Mean Worm Burden + SE | % Reduction Versus Control | Mean No. of Larvae in Lungs |
|---|---|---|---|
| Control (N = 5) | 59 ± 8 | — | 2 |
| JH$_3$(N = 5) | 20 ± 3 | 66 | 15 |

EXAMPLE 6

We fed nymphs and adults of the blood sucking Argasid tick, *Ornithodoros moubata*, on 50 mice immunized with JH$_3$-KLH, with beta-ecdysone-KLH, or with KLH only as control. The mice were bled at the time intervals described above.

Table 6 describes the effect on immunized and control mice, of feeding nymphs of *O. moubata* to the mice. We observed a statistically significant reduction in the moulting of first stage nymphs fed blood containing anti-JH$_3$ or anti-betaecdysone antibodies (p<0.01).

TABLE 6

| Immunization | No. of First Stage Nymphs (N1) | Mean % Moulting N1 N2 |
|---|---|---|
| Control | N = 80 | 96 ± 3 |
| JH$_3$ | N = 124 | 63 ± 3 |
| beta-ecdysone | N = 117 | 78 ± 5 |

EXAMPLE 7

We fed nymphs and adults of the Ixodid tick, *Riphicephalus sangineus*, on 5 rabbits immunized with JH$_3$—KLH or Ecdysterone-KLH as illustrated for mice, above. The rabbits were bled at the time intervals described above.

Table 7 illustrates the effect of feeding female *R. sangineus* on JH$_3$—KLH or beta-ecdysone-KLH immunized rabbits. We observed a significantly reduced hatch of larvae from those eggs.

TABLE 7

| Immunization | Mean No. Eggs Per Female | % Hatch |
|---|---|---|
| Control | 3211 | 98.3% |
| JH$_3$ | 2925 | 79.9% |
| beta-ecdysone | 3939 | 14.2% |

EXAMPLE 8

This example illustrates the effect of the number of hormone molecules coupled to the carrier upon the amount of antibody produced to the hormone. Juvenile hormone immunogens as prepared by the conjugation methods described in Example 1 and beta-ecdysone (beta-E) immunogens are prepared by the methods described in Example 3 above. Four different $JH_3$—BSA immunogens were prepared so that less than 3,3,10, or 19 $JH_3$ molecules respectively, were coupled to each BSA molecule (on a basis of $10^5$ daltons molecular weight per BSA molecule). Stated differently $JH_3$—BSA immunogens were prepared with ratios of $JH_3$ to BSA of less than 3;1, 3:1, 10:1 and 19:1 hormone to carrier coupling.

Similar beta-ecdysone-BSA immunogens were prepared with coupling ratios of 8:1 or 20:1 of the hormone per molecule of BSA ($10^5$ daltons molecular weight basis).

Mice were immunized four times at approximately one month intervals with 500 μg of each $JH_3$—BSA or beta-ecdysone-BSA preparations. The initial immunization was given intraperitoneally in Freunds Complete Adjuvant. The three remaining injections were given in physiologic saline, alternating between subcutaneous and intraperitoneal sites. Two weeks after the second, third and fourth injections, blood was drawn from each mouse and the serum collected.

Each serum was assayed for anti-$JH_3$ antibodies utilizing the ELISA technique with $JH_3$—DT or beta-E-DT or as test antigen and by a direct antigen binding radioimmunoassay (RIA) in which tritium labeled radioactive $JH_3$ or alpha-ecdysone was used as the test antigen. Alpha-ecdysone is preferentially used as the radioactive antigen because there is a high cross-reactivity between anti-beta-ecdysone antibodies and alpha-ecdysone antigen and because alpha-ecdysone is readily available in radiolabelled form. The amount of antibody produced was expressed by the end point dilution method for ELISA and by the number of picograms of radioactive $JH_3$ or alpha-ecdysone directly bound per microliter of anti-$JH_3$ or beta-ecdysone serum from immunized animals in the RIA.

Table 8 illustrates the effect of coupling of less than 3, 3, 10 and 19 $JH_3$ molecules to each BSA molecule and the coupling of 8 and 20 beta-E molecules on each BSA molecule upon the antibody response after four injections of each of these antigens. In both examples of $JH_3$ and beta-ecdysone coupled at varying ratios to BSA, the greatest antibody responses were measured in animals immunized with the conjugates coupled at the highest hormone to carrier ratios.

TABLE 8

| $JH_3$:BSA coupling (per $10^5$ daltons of BSA) | ELISA Titer (Endpoint Dilution) | RIA Titer (pg $JH_3$/ul serum) Mean ± SE |
| --- | --- | --- |
| Less than 3:1 | 0 (Negative) | 0.00 |
| 3:1 | 1:100 | 0.75 ± 0.32 |
| 10:1 | 1:1,000 | 1.15 ± 0.61 |
| 19:1 | 1:10,000 | 1.04 ± 0.64 |
| Beta-ecdysone: BSA coupling | | (pg. beta-E/ul serum) |
| 8:1 | 1:100 | 0.33 ±]0.17 |
| 20:1 | 1:100,000 | 32.3 ± 9.3 |

EXAMPLE 9

This example illustrates the effect that the coupling of $JH_3$ or beta-ecdysone to different protein carriers has upon the antibody response of the immunized animals to these hormones. Conjugates prepared by the methods described in Example 1 and Example 3 above were injected into mice as described in Example 8. Because the protein species used vary greatly in molecular weight, the coupling ratios are expressed in number of hormone molecules coupled per $10^5$ daltons molecular weight of protein. Antibody responses were measured as described in Example 8.

Table 9 demonstrates the effect of the different carriers tested upon the antibody response to $JH_3$ or beta-ecdysone. In the case of $JH_3$—BSA and $JH_3$—KLH conjugates, a better antibody response to $JH_3$ was observed in $JH_3$—KLH immunized animals by both ELISA and RIA assays. In the instance of beta-ecdysone-BSA or -DT conjugates, a better response to the hormone was shown by the RIA assay to occur in animals immunized with the DT conjugates.

TABLE 9

| Protein Carrier (Hormone Coupling ratio) | ELISA Titer (Endpoint Dilution) | RIA Titer (pg hormone bound/ul serum) Mean ± SE |
| --- | --- | --- |
| $JH_3$-BSA (28:1) | 1:10,000 | 1.04 ± 0.62 |
| $JH_3$-KLH (32:1) | 1:10,000,000 | 6.65 ± 1.12 |
| Beta-Ecdysone-BSA (30:1) | 1:100,000 | 32.3 ± 9.3 |
| Beta-Ecdysone-DT (27:1) | 1:100,000 | 150 ± 31 |

EXAMPLE 10

In this example we illustrate one embodiment of our method wherein animals are immunized with a combination of invertebrate hormones to induce antibodies to the components of the combination. Mice were immunized with a mixture consisting of equal portions of $JH_3$—KLH and beta-ecdysone-KLH (500 μg total conjugate) by the method described in Example 8. Rabbits were immunized in a similar manner, except that each rabbit received 500 μg of each conjugate component, instead of 250 μg.

Table 10 lists the ELISA titers produced to each hormone in mice, and the ELISA and RIA titers in rabbits after four immunizations, demonstrating that an immunogen containing the two hormones induces a specific antibody response to both.

TABLE 10

| Hormone | ELISA Titer (Endpoint Dilution) | RIA Titer (pg hormone bound/ul serum) Mean ± SE |
| --- | --- | --- |
| Mice | | |
| $JH_3$ | 1:100,000 | Not Done |
| Beta-Ecdysone | 1:1,000 | Not Done |
| Rabbits | | |
| $JH_3$ | 1:1,000 | 1.0 ± 0.3 |
| Beta-Ecdysone | 1:1,000 | 6.5 ±0.2 |

EXAMPLE 11

In this example we demonstrate the effect of passive administration of monoclonal antibodies specific for $JH_3$ and beta-ecdysone to mice upon the mean worm burden resulting in these mice after challenge with two nematode parasites, *Nematospiroides dubius* and *Trichinella spiralis*.

Individual mice were injected intravenously on three consecutive days with approximately 500 μg of either three different monoclonal antibodies specific for free $JH_3$ hormone or three different monoclonal antibodies specific for beta-ecdysone. Mice receiving both $JH_3$ and beta-ecdysone specific monoclonal antibodies were injected with 250 μg of each monoclonal on three consecutive days. After the third injection of antibody, mice were challenged with 200–250 infective $L_3$ larvae of *N. dubius* or 200 infective $L_1$ of *T. spiralis*. After 10 days (*N. dubius*) or 7 days (*T. soiralis*) we euthanized the mice and counted the number of worms present in the small intestine.

Table 11 demonstrates that mice immunized with either $JH_3$ or beta-ecdysone monoclonal antibodies, either singly or in combination, experienced reduced worm burdens when compared to non-immunized control mice.

TABLE 11

| Animal Group (N = 10 mice) | Monoclonal Antibody (ELISA Titer) | Worm Burden ± SE (Living Adult Worms Present in Intestine) |
|---|---|---|
| *N. dubius* Control | None | 279 ± 18 (10 days) |
| *N. dubius* $JH_3$ | JH3 (1:100,000) | 234 ± 20 (10 days) |
| *T. spiralis* Control | None | 211 ± 17 (7 days) |
| *T. spiralis* $JH_3$ | $JH_3$(1:100,000) | 146 ± 23 (7 days) |
| *T. spiralis* Beta-Ecdysone | Beta-Ecdysone (1:100,000) | 181 ± 16 (7 days) |
| *T. spiralis* $JH_3$ + Beta-Ecdysone | $JH_3$ (1:10,000) Beta-Ecdysone (1:10,000) | 148 ± 15 (7 days) |

EXAMPLE 12

As described in Example 8 and 9, we have determined that the effectiveness of an invertebrate hormone-protein carrier in inducing an anti-hormone specific immune response is dependent upon both the protein species making up the carrier and the coupling ratio of the hormone to the carrier. In this example, we illustrate the effects of immunization of mice with $JH_3$ coupled at high ratios to different protein carriers upon the resulting worm burdens after *T. spiralis* challenge. More were immunized with $JH_3$—BSA or $JH_3$—KLH as described in Example 8 and challenged with *T. spiralis* as described in Example 11.

Table 12 demonstrates that the $JH_3$—KLH conjugates coupled at a 32:1 ratio (molecules of $JH_3$ per $10^5$ daltons molecular weight of carrier) produced greater immune responses in mice and resulted in larger *T. spiralis* worm burden reductions then that which occurred in mice immunized with $JH_3$—BSA conjugates coupled at a 28:1 ratio. Thus, mice immunized with $JH_3$—KLH experienced an average reduction of worm burden of 40%, while $JH_3$—BSA mice experienced a 1% reduction of worm burden.

TABLE 12

| Conjugate | Elisa Response | RIA Titer ± SE | *T. spiralis* burden ± SE |
|---|---|---|---|
| BSA only Control | 0 | 0 | 149 ± 16 |
| $JH_3$-BSA (28:1) | 1:10,000 | 1.04 ± 0.62 | 147 ± 13 |
| KLH only Control | 0 | 0 | 185 ± 18 |
| $JH_3$-KLH | 1:10,000,000 | 6.65 ± 1.12 | 111 ± 12 |

TABLE 12-continued

| Conjugate | Elisa Response | RIA Titer ± SE | *T. spiralis* burden ± SE |
|---|---|---|---|
| (32:1) | | | |

EXAMPLE 13

In this example, a method for coupling single hormone molecules to spacer molecules is described. This embodiment of the invention represents an alternative method of hormone coupling to that in Example 1, in which the presence of the spacer molecule induces a new spatial relationship between the hormone and the carrier protein. This alteration in spatial relationship alters presentation of the hormone to the immune system, resulting in production of a wider variety of antibodies with specificity for the hormone.

Any molecule which is capable of being linked to JH, beta-ecdysone, or other invertebrate hormones can be used as the spacer molecule. These include, but are not limited to, small peptides such as hexaproline, trialanine and triglycine; aromatic benzene derivatives such as 2,(4, aminophenyl)-ethylamine; small aliphatic hydrocarbon molecules such as 6-aminohexanoic acid; anhydrides such as succinic anhydride; and the class of cross-linking compounds known to the art as heterobifunctional reagents e.g. m-maleimidobenzoyl-N-hydroxysuccinimide ester.

As an example of this method, we have prepared $JH_3$—hexaproline spacered conjugates. Initially we prepared the $JH_3$—NHS activated ester as described in Example 1. The activated ester of $JH_3$ was dissolved in 1.0 ml of carbon tetrachloride to which had been added enough hexaproline to make it equimolar to the amount of $JH_3$—NHS added. The mixture was incubated overnight to permit coupling of the $JH_3$ to the hexaproline. Excess DCCI, NHS and dicyclohexylurea is removed as described in Example 1. Subsequently, we activated the terminal carboxyl group of the hexaproline with DCCI and NHS in carbon tetrachloride to produce the activated ester of $JH_3$-hexaproline (as described for producing the ester of $JH_3$ in Example 1). After removal of contaminating excess DCCI, NHS and dicyclohexylurea, the $JH_3$-hexaproline activated ester is reacted with a selected protein carrier to produce conjugates coupled at the desired hormone to protein molar ratio as described in Example 1.

Table 13 demonstrates the induction in mice of anti-$JH_3$ specific antibodies by $JH_3$-hexaproline-BSA conjugates. The BSA conjugates were coupled at a ratio of approximately 20 moles $JH_3$:1 mole BSA. Mice were immunized four times with 250 μg of conjugate and assayed for antibody as described in Example 8.

TABLE 13

| ELISA Response (Endpoint Dilution) | RIA Response (pg hormone bound/ul Serum) Mean ± SE |
|---|---|
| 1:100,000 | 1.02 ± 0.1 |

EXAMPLE 14

Example 14 describes a method by which the number of JH or beta-Ecdysone molecules coupled to a particular site on the protein can be increased. In this embodiment increasing the number of hormone molecules at a particular conjugation point increases the likelihood that a hormone specific antibody producing B lymphocyte population will react with the hormone and thus be stimulated to produce larger quantities of antibody than otherwise would be produced. In this embodiment the spacer compound is a compound comprising a plurality of functional groups, e.g. hydroxyl or amino groups, to which the endocrine product or hormone can be bound. Thus a plurality of hormone molecules are attached to the spacer molecule which in turn is coupled to the immunogenic protein carrier. The preferred functional group in each case will depend upon the particular hormone which is to be bound to the spacer molecule and the chemical groups on the hormone molecule that are to be bound to the functional group.

One preferred method of this embodiment is to conjugate JH to gallic acid (3,4,5 trihydroxybenzoic acid) or to polyvinyl alcohol (PVA) by producing an acid chloride intermediate of $JH_3$. We dissolve, for example, 4 umoles of $JH_3$-acid (containing $10^5$ CPM of tritium labelled $JH_3$-acid radioisotope) in carbon tetrachloride and add a molar equivalent amount of triphenylphosphine. After 4 hours of incubation, the mixture is centrifuged or filtered to remove precipitated triphenylphosphine oxide and the supernatant containing $JH_3$-acid chloride is removed and dried under a dry $N_2$ stream. The residue is dissolved in 2 mls of hexane and centrifuged or filtered to remove additional insoluble triphenylphosphine oxide. The hexane containing $JH_3$-acid chloride is removed to a clean container and the hexane is evaporated off under a dry $N_2$ stream. The residue is redissolved in hexane and the centrifugation or filtration step is repeated if any insoluble triphenylphosphine oxide is detected. The hexane is evaporated off under a dry $N_2$ stream and the $JH_3$-acid chloride residue is reacted with molecules containing multiple hydroxyl groups as described below.

Four umoles of $JH_3$-acid chloride and one umole of gallic acid are dissolved in 2 mls of pyridine and reacted for 4 hours to form the tri- or di- $JH_3$ benzyl ester of gallic acid.

The $JH_3$-gallic acid complex is extracted from unreacted $JH_3$-acid chloride by addition of 0.1 M aqueous sodium bicarbonate and a nonpolar organic solvent such as diethyl ether in equal amounts to the above reaction mixture. The $JH_3$-gallic acid complex selectively partitions into the nonpolar organic solvent phase and is recovered without further purification by removing the diethylether phase from the aqueous phase and by evaporating off the organic solvent under an $N_2$ stream in a tared vial. After weighing the residue, the average number of $JH_3$ acid residues linked to each gallic acid molecule is determined by the isotopic dilution method.

The activated ester of the carboxyl group of the $JH_3$-gallic acid complex is prepared in a manner similar to that described for JH acid in Example 1. The $JH_3$-gallic acid is dissolved or suspended in a small volume (1 ml) of an appropriate polar organic solvent, such as THF. A slight molar excess of DCCI dissolved in THF/pyridine is added and the mixture is incubated for one hour with stirring at room temperature. A slight molar excess of NHS is added to the above mixture and the new mixture is incubated overnight at room temperature. Inactivation and removal of excess DCCI, NHS and the insoluble dicyclohexylurea product is accomplished as described in Example 1. The extracted active ester is dried under $N_2$, weighed and redissolved in an appropriate polar organic solvent such as THF. Enough of the activated ester of $JH_3$-gallic acid is mixed with carrier protein dissolved in 0.15 M NaCl solution or a similar aqueous medium to achieve coupling ratios of from about 3 to about 40 molecules $JH_3$-gallic acid complex to each $10^5$ daltons molecular weight of protein carrier. Determination of the number of amino groups on the protein carrier substituted with $JH_3$-gallic acid molecules is determined by the TNBS or fluorescamine methods as described in Example 1.

Mice or other animals are immunized with the conjugates as described in Example 8.

The JH-acid chloride intermediate methodology was also used to prepare multiple $JH_3$ substituted molecules of polyvinyl alcohol (PVA), and may be used for other similar molecules including sugars, and other carbohydrates. PVA consists of linear $-CH_2-CH(OH)-$ subunits which vary in number according to the molecular weight of the PVA molecule (i.e. PVA, M.W. 2000 contains approximately 45 $-OH$ groups). $JH_3$—acid chloride is coupled to PVA by incubating the reactants together in pyridine or another suitable organic solvent containing a small amount of pyridine for 1 hour.

The molecular form of PVA used may be selected from those varying in molecular weight between 2,000-20,000, with the lower molecular weight species being preferred. $JH_3$ acid chloride is added at ratios varying between 10 molecules to 40 molecules per molecule of PVA. By using radiolabelled $JH_3$, the moles of $JH_3$ coupled to a mole of PVA may determined by the isotopic dilution method.

Coupling of the $JH_3$-substituted PVA molecules to a carrier protein is accomplished by activating at least one non-coupled- OH residue of each PPVA molecule by the succinylation reaction as described in Example 3. Subsequent coupling of the $JH_3$—PVA-succinate molecular complex to the carrier protein is completed by the activated ester method (Example 1) or mixed anhydride method (Example 3). The number of PVA molecules coupled to each protein carrier molecule may be determined by the methods described in Example 1 that measure free amino groups.

Mice or other animals are immunized with the conjugates as described in Example 8.

EXAMPLE 15

Monoclonal antibodies (Mabs) to $JH_1$, $JH_2$, $JH_3$ and beta-ecdysone were produced by hybridoma technology as described in Example 4. In order to characterize the hormone binding characteristics of the anti-$JH_3$ and anti-beta ecdysone Mabs, we have reacted them with forms of $JH_3$ or Beta-ecdysone antigens that are either free in solution or forms of the hormones that were linked to a carrier molecule by the methods of Example 1 or Example 3.

These antigen binding assays of Mabs are useful in characterizing the specificity of the polyclonal anti-hormone antibody response expected to be induced in immunized animals by the immunogens produced using the methods of conjugation of Example 1 and Example 3. The specificity of the response, in turn, is indicative of the amount or degree of biologic effect that an animal immunized with an immunogen produced by the methods of Example 1 or Example 3 exerts upon a target invertebrate parasite. (The biologic effect can occur in the forms of death of the parasite, inhibition of development, or inhibition of reproduction). In particular, if a Mab reacts in the antigen binding assays with only the conjugated form of the hormone and not with the free hormone form, that antibody may not bind free hormone as it is found in the target parasite. Thus, antibodies with such specificity (conjugated hormone only) may have no biologic activity against parasites. Conversely, antibodies that bind the free form of the hormone in the antigen assays may bind the hormone as it occurs in the parasite and, consequently, exert biologic effect upon the parasite.

Free hormone binding Mab assays were completed by a method known to those skilled in the art as a direct antigen binding radioimmunoassay. Assays of binding of Mabs to conjugated hormone were carried out by the ELISA technique.

All anti-beta-ecdysone Mabs tested reacted with antigen in both the free hormone and the conjugated hormone assays. Thus, the polyclonal antibody response to Beta-Ecdysone in immunized animals should produce a consistent and high level biologic effect upon the target parasite.

We assayed eight anti-JH$_3$ Mabs for free hormone and conjugated hormone binding activities. Four antibodies bound free JH$_3$ hormone (as well as conjugated hormone) and 4 bound only conjugated hormone. Thus, anti-JH$_3$ Mabs expressed two types of antigen binding specificity. These have been designated Type 1 and Type 2 anti-JH$_3$ reactivity antibodies, respectively. Table 15 summarizes several characteristics of Type 1 and Type 2 antibodies that have been determined and are central to the present invention.

Hybridoma cell lines producing monoclonal antibodies which react with free JH$_3$ and Beta-ecdysone hormones have been deposited with the American Type Culture Collection, 12301 Parklawn Drive, Rockville, MD. 20852, USA, pursuant to the provisions of the Budapest Treaty and have been assigned accession Nos. ATCC HB 9529 and ATCC HB 9530 respectively.

TABLE 15

| Comparison of Type 1 and Type 2 anti-JH$_3$ Monoclonal Antibodies | | |
|---|---|---|
| Activity | Type 1* | Type 2* |
| Bind free JH$_3$ hormone antigen | ++++ | 0 |
| Bind conjugated JH$_3$ hormone antigen | ++++ | ++++ |
| Relative Level in Serum | + | ++++ |
| Have biologic effect upon target parasites | ++++ | 0 |

*+ indicates the relative levels of binding; serum level; and biological effect.

The most important characteristic of Type 1 antibodies in relation to this invention are the low quantities produced in animals immunized by conjugates produced by the methods described in Example 1 and their function as the antibodies exerting the biologic effects against target parasites. Thus, several embodiments of this invention are designed to improve the Type 1 anti-JH$_3$ antibody response.

As an example of the importance of the Type 1 anti-JH$_3$ response, we have compared the *T. spiralis* worm burden reductions in mice to the ability of the sera of these mice to bind free JH$_3$. Table 16 compares the mean reduction in worm burdens in mice exhibiting JH$_3$ free hormone antigen binding of up to 1.5 pg of JH$_3$/μl of serum to the worm burden reduction in mice binding 1.5-15 pg/μl of $JH_3$ free hormone antigen.

TABLE 16

| $JH_3$ Binding pg/ul serum | Mean Worm Burden Reduction versus Control Mice (Range) |
|---|---|
| Up to 1.5 pg/ul | 25% (14-39%) |
| 1.5 to 15 pg/ul | 57% (32-90%) |

EXAMPLE 16

This example illustrates a means by which internal images of invertebrate hormones may be used to produce a vaccine capable of eliciting antibody responses to the hormone. In broad outline, animals, e.g. mice, are immunized against JH or Ecdysones coupled to an immunogenic carrier as described in Example 1, Example 3 or Example 14. After it is verified that the mice are producing antibody to the hormone, a cell fusion is performed to produce hybridomas secreting anti-hormone antibody as described in Example 4. The monoclonal anti-hormone antibodies are coupled to an immunogenic carrier and injected into mice to induce anti-idiotypic antibodies. A cell fusion is then performed to produce monoclonal anti-idiotypic antibodies, from which are selected those monoclonal antibodies that express immunogenic internal images of the hormone, e.g. JH or Ecdysone. Finally, internal image antibodies are utilized as immunogens to induce anti-JH or anti-Ecdysone specific antibodies in animals, e.g. rabbits.

As a specific example of this method, anti-$JH_3$ monoclonal antibodies (Mabs) are coupled to KLH carrier by using glutaraldehyde as the coupling agent. Mice are immunized by intraperitoneal injection of 100 μg of conjugate emulsified in Freunds Complete Adjuvant (FCA), followed by 3 booster injections in saline at monthly intervals. To ascertain that those immunized mice are producing internal images of $JH_3$ their sera are assayed for the ability to block the binding of $JH_3$ to anti-$JH_3$ Mabs by a radioimmunoassay. Mice whose sera inhibit $JH_3$ binding to anti-$JH_3$ Mabs are chosen for hybridoma fusions to isolate anti-anti-id (internal image) Mabs. Such Mabs are identified by their ability to block the binding of $JH_3$ (id) to anti-$JH_3$ Mabs (anti-id).

Mab lines exhibiting internal image characteristics are further tested by determining their ability to induce anti-$JH_3$ antibody responses in rabbits. Rabbits are immunized with mixtures of up to 10 of the potential internal image containing Mabs. Each rabbit is injected with 100 μg of the mixture in FCA followed by 3 additional injections of 100 μg of antibody in saline at 2 week intervals. Blood is drawn from each rabbit every two weeks and processed for serum. Assays for anti-$JH_3$ antibodies in the sera are run by the ELISA or direct antigen binding RIA.

While we have presented a number of embodiments of this invention, it is apparent that our basic construction can be altered to provide other embodiments which utilize the processes and compositions of this invention. Therefore, it will be appreciated that the scope of this invention is to be defined by the appended claims rather than by the specific embodiments which have been presented by way of example.

What is claimed is:

1. A pharmaceutical composition for use in a vertebrate host as a vaccine or a medicament for immunizing against or treating for infection by an invertebrate ectoparasite or endoparasite comprising an immunogen that is capable of eliciting antibodies in the host that bind to the native form of juvenile hormone or beta-ecdysone and have a biological effect on the ectoparasite or endoparasite, wherein the immunogen comprises an endocrine product of the ectoparasite or endoparasite selected from the group consisting of juvenile hormone, beta-ecdysone or analogs thereof, conjugated to a protein selected from the group consisting of mino acids or chains of amino acids, straight chain hydrocarbons, aromatic derivatives, gallic acid, or polyvinyl alcohol carrier by means of a spacer molecule and a pharmaceutically acceptable carrier.

2. A method of immunizing a vertebrate against or treating a vertebrate for infection by endoparasites or ectoparasites comprising administering to the vertebrate an immunologically effective amount of a composition of claim 1.

3. A pharmaceutical composition for use in a vertebrate host as a vaccine or a medicament for immunizing against or treating for infection by an invertebrate ectoparasite or endoparasite comprising an immunogen that is capable of eliciting antibodies in the host that bind to the native form of juvenile hormone or beta-ecdysone and have a biological effect on the ectoparasite or endoparasite, wherein the immunogen comprises an endocrine product of the ectoparasite or endoparasite selected from the group consisting of juvenile hormone, beta-ecdysone or analogs thereof, conjugated to keyhole limpet hemocyanin, and a pharmaceutically acceptable carrier.

4. A pharmaceutical composition for use in a vertebrate host as a vaccine or a medicament for immunizing against or treating for infection by an invertebrate ectoparasite or endoparasite comprising an immunogen that is capable of eliciting antibodies in the host that bind to the native form of juvenile hormone or beta-ecdysone and have a biological effect on the ectoparasite or endoparasite, wherein the immunogen comprises an endocrine product of the ectoparasite or endoparasite selected from the group consisting of juvenile hormone, beta-ecdysone or analogs thereof, conjugated to diphtheria toxoid, and a pharmaceutically acceptable carrier.

5. A pharmaceutical composition for use in a vertebrate host as a vaccine or a medicament for immunizing against or treating for infection by an invertebrate ectoparasite or endoparasite comprising an immunogen that is capable of eliciting antibodies in the host that bind to the native form of juvenile hormone and have a biological effect on the ectoparasite or endoparasite, wherein the immunogen comprises juvenile hormone, or analogs thereof, conjugated to a protein carrier by means of a spacer molecule of gallic acid, and a pharmaceutically acceptable carrier.

6. A method of immunizing a vertebrate against or treating a vertebrate for infection by an ectoparasite or endoparasite comprising administering to the vertebrate an immunologically effective amount of a first immunogen comprising juvenile hormone or an analog thereof conjugated to a protein carrier and an immunologically effective amount of a second immunogen comprising beta-ecdysone or an analog thereof conjugated to a protein carrier.

7. A pharmaceutical composition for use in a host vertebrate as a vaccine or medicament for immunizing against or treating for infection by invertebrate endoparasites or ectoparasites comprising an immunologically effective amount of antibodies produced from hybridomas of the cell line ATCC 9529 which specifically bind to the native form of juvenile hormone and a pharmaceutically acceptable carrier.

8. A method of immunizing a vertebrate against or treating a vertebrate for infection by endoparasites or ectoparasites comprising administering to the vertebrate an immunologically effective amount of a composition of claim 7.

9. A pharmaceutical composition for use in a host vertebrate as a vaccine or medicament for immunizing against or treating for infection by invertebrate endoparasites or ectoparasites comprising an immunologically effective amount of antibodies produced from hybridomas of the cell line ATCC 9530 which specifically bind to the native form of beta-ecdysone and a pharmaceutically acceptable carrier.

10. A method of immunizing a vertebrate against or treating a vertebrate for infection by endoparasites or ectoparasites comprising administering an immunologically effective amount of the composition of claim 9.

11. A method of immunizing a vertebrate against or treating a vertebrate for infection by endoparasites or ectoparasites comprising administering to the vertebrate an immunologically effective amount of a first composition comprising antibodies that specifically bind to the native form of juvenile hormone and an immunologically effective amount of a second composition comprising antibodies that specifically bind to the native form of beta-ecdysone.

* * * * *